(12) United States Patent
Lee

(10) Patent No.: US 6,528,678 B2
(45) Date of Patent: Mar. 4, 2003

(54) PHOSGENE-FREE PROCESS FOR PREPARING CARBAMATES

(75) Inventor: Byung H. Lee, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/000,756

(22) Filed: Oct. 24, 2001

(65) Prior Publication Data

US 2002/0120140 A1 Aug. 29, 2002

Related U.S. Application Data

(60) Provisional application No. 60/243,047, filed on Oct. 25, 2000.

(51) Int. Cl.[7] ............................................. C07C 271/00
(52) U.S. Cl. ........................................... 560/24; 560/32
(58) Field of Search ...................... 560/24, 32

(56) References Cited

FOREIGN PATENT DOCUMENTS

| EP | 0 511 948 A2 | 11/1992 |
|---|---|---|
| EP | 0 511 948 B1 | 11/1992 |
| WO | WO 00/50389 A1 * | 8/2000 |

OTHER PUBLICATIONS

A Convenient Method for the Synthesis of Carbamate Esters from Amines and Tetraethylammonium Hydrogen Carbonate, by Achille INESI et al., *J. Org. Chem.* 1998, 63, pp. 1337–1338.

* cited by examiner

*Primary Examiner*—Deborah D. Carr
*Assistant Examiner*—Bul A. Zucker
(74) *Attorney, Agent, or Firm*—Flynn, Thiel, Boutell & Tanis, P.C.

(57) ABSTRACT

A phosgene-free method for preparing a carbamate from a compound containing an amine group involves reacting the compound with an alkylating agent in the presence of carbon dioxide and cesium carbonate. A reaction can take place under standard pressure and temperature conditions and produces carbamates in a high yield with low by-product formation.

8 Claims, No Drawings

PHOSGENE-FREE PROCESS FOR PREPARING CARBAMATES

This application claims benefit of provisional application No. 60/249,047 filed Oct. 25, 2000

FIELD OF THE INVENTION

The present invention is directed to a method for preparing a carbamate from a compound containing an amine group.

BACKGROUND OF THE INVENTION

Carbamates have been used as a blocking group for the amino function of α-amino acids since the benzyloxycarbonyl group was used in 1932 by Bergmann and Zervas. Traditionally, the most important route for the synthesis of carbamates involves the use of phosgene/isocyanate technology. However, given the toxicity of phosgene and the environmental concerns associated therewith, a safer and more convenient method of providing a carbamate blocking group has been sought.

Recently, carbon dioxide has been proposed as an alternative for phosgene in the production of carbamates from amines. Carbon dioxide has been used to prepare carbamates with amines in the presence of electrophiles such as 2-bromoalkaphenols, epoxides, alkyl halides and alkynes. Recently, carbamates have been prepared using amines, carbon dioxide at a pressure of from 80 to 160 psig, alkylchlorides and sterically hindered organic bases such as pentaalkylguanidines. Rossi et al in *J.Org.Chem.* 1998, 63, 1337, reported a mild procedure for synthesizing carbamates through the reaction of amines and alkyl halides in the amount of five equivalents with tetraethylammonium hydrogen carbonate, prepared from tetraethylammonium hydroxide and carbon dioxide. However, this reaction was very sluggish and required the amount of five equivalents of the alkyl halide. Therefore, there still exists a need for a method for preparing carbamates from amines which is safe, economical and capable of producing carbamates in an efficient manner.

SUMMARY OF THE INVENTION

The present invention is directed to a method for preparing a carbamate from a compound containing an amine group in which the compound is reacted with an alkylating agent in the presence of carbon dioxide and cesium carbonate. In the inventive method, the reaction can take place at ambient or standard temperatures and pressures to produce the desired carbamate at a high yield without the use of dangerous phosgene gas.

DETAILED DESCRIPTION OF THE INVENTION

The present invention provides a safe and simple method for attaching a carbonate group to amines and amino acids and for preparing other carbamates by reacting a primary or secondary amine group with carbon dioxide, cesium carbonate and an alkylating group at ambient temperature and pressure. The reaction preferably takes place in a polar aprotic solvent such as dimethylformamide and, unexpectedly, high yields of the carbamate product are obtained when cesium carbonate is present in the reaction system. The compound containing the amine group is not especially limited and can be an amino acid or any other organic compound containing at least one of a primary or a secondary amine group. Likewise, the alkylating agent is not especially limited and can be an organic compound containing a halide such as benzylchloride or chloromethyl pivalate. In the present invention, the presence of cesium carbonate in the reaction system enables the product carbamate compound to be obtained in a high yield with a low amount of by-product formation.

The advantages of the present invention are further exemplified by the following Examples and Comparative Examples.

EXAMPLE 1

A benzyloxy carbonyl (Cbz) group was added to phenylpiperazine according to the following reaction scheme.

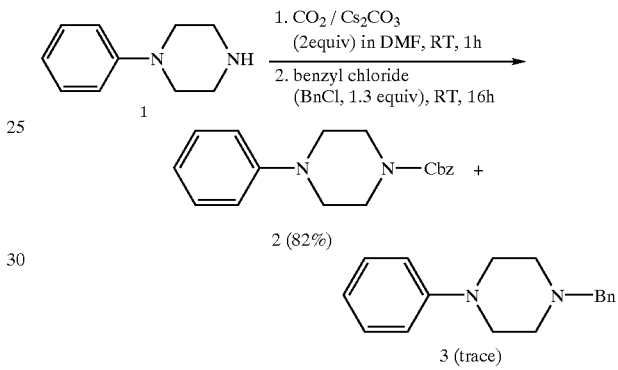

Compound 1 (162 mg, 1.0 mmol) was dissolved in 35 ml of dimethylformamide and 652 mg of cesium carbonate (2.0 mmol) added thereto. 13 grams of solid carbon dioxide in the form of a cylindrical piece of dry ice was added thereto and the flask immediately capped with a balloon which rapidly inflated with the carbon dioxide. The reaction mixture was stirred for about 60 minutes before adding 166 mg of benzylchloride (1.3 mmol) dissolved in 1 ml of dimethylformamide thereto. The reaction mixture was stirred over night at room temperature and then cooled to 0° C. Water was added to the point of cloudiness and the mixture extracted with diethylether (typically 2×80 ml). The extracts were combined and concentrated in vacuo in a rotary evaporator. The residual dimethylformamide was removed under a high vacuum with gentle warming. The crude product thus obtained was purified by preparative thin-layer chromatography (silica gel, 1:3 ethyl acetate/hexane) to give 240 mg of product 2 as an oil in an 82% yield. The alkylated by-product 3 was obtained only in a trace amount. H NMR (400 MHz CDCl$_3$) δ 3.17 (in, 4H), 3.68 (in, 4H), 5.19 Cs, 2H), 6.93 (in, 3H), 7.3–7.5 (in, 7H); MS (ES+); m/z 297 CM+H), 319 (M+Na).

In order to illustrate the importance of cesium carbonate being present, the identical reaction discussed above was performed using various other bases. None of these various other bases were as successful in generating the carbamate product as cesium carbonate. The results are shown in Table 1.

TABLE 1

Effect of Base on Carbamate Formation from 1, Carbon Dioxide and Benzyl Chloride

| | Base | Product 2 (% yield) | Product 3 (% yield) |
|---|---|---|---|
| Example 1 | $Cs_2CO_3$ | 82 | trace |
| Comparative Example 1 | $BaCO_3$ | — | 90 |
| Comparative Example 2 | $Ba(OH)_2$ | — | 100 |
| Comparative Example 3 | $ET_3N$ | — | 100 |
| Comparative Example 4 | DBU | — | 100 |
| Comparative Example 5 | $Na_2CO_3$ | 33 | 12 |
| Comparative Example 6 | $K_2CO_3$ | 5 | 20 |
| Comparative Example 7 | $Rb_2CO_3$ | 10 | 68 |

The use of a simple tertiary amine, triethylamine, gave no conversion to the carbamate and other bases such as barium carbonate and barium hydroxide gave the undesired by-product 3 exclusively. The Group IA metal carbonates yielded more carbamate product 2 than the Group IIA metal carbonates. The bulkier metal carbonates (Group IA) tended to give more carbamate product 2. In the present invention, it is believed that the lower charge density of the cesium cation allows for a more exposed carboxylate anion makes it a better nucleophile with the result that the alkylation of the oxygen anion occurs preferentially to that of the amine. The above methodology was also used to prepare benzyloxycarbonyl-protected amino acids in yields of from 53 to 86% as shown in Table 2.

TABLE 2

Formation of Cbz-Amino Acids from Amino Acids, Carbon Dioxide, and Benzyl Chloride

| Substrate | Product | % yield |
|---|---|---|
| H-Pro-OBn | Cbz-Pro-OBn | 86 |
| H-Phe-OBn | Cbz-Phe-OBn | 75* |
| H-Ala-O$^t$Bu | Cbz-Ala-O$^t$Bu | 72 |
| H-Tyr-OBn | Cbz-Tyr-OBn | 53* |
| H-Ser-OBn | Cbz-Ser-OBn | 75* |

*Based on recovered starting material.

The method of the present invention is not limited to the preparation of benzyloxycarbonyl-protected amines. By choosing an appropriate alkylating agent, the inventive chemistry can be used for the preparation of pro-drugs as shown in Example 2 below.

EXAMPLE 2

As shown in the below reaction scheme, phenylpiperazine was formed into a carbamate according to the present invention using chloromethyl pivalate as the alkylating agent.

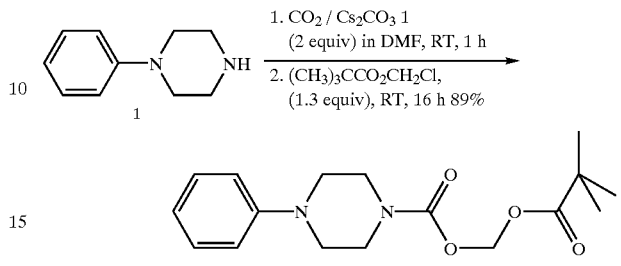

Phenylpiperazine 1 was stirred with two equivalents of cesium carbonate and dry ice (solid carbon dioxide) and dimethylformamide for 60 minutes at room temperature. 1.3 equivalents of chloromethyl pivalate was added thereto and the mixture stirred over night to produce the pro-drug compound 4 in an 89% yield.

The present invention provides a convenient method for synthesizing carbamates from primary and secondary amines by conducting a reaction at ambient temperature and pressure using carbon dioxide, cesium carbonate and an alkylating agent. The method of the present invention provides carbamates in high yields without a necessity of pressurized carbon dioxide, large excesses of alkylating agents for elevated temperatures.

What is claimed is:

1. A method for preparing a carbamate from a compound containing an amine group comprising reacting the compound with chloromethyl pivalate in the presence of carbon dioxide and cesium carbonate.

2. The method of claim 1, wherein said compound contains a primary amine group.

3. The method of claim 1, wherein said compound contains a secondary amine group.

4. The method of claim 1, wherein said compound is an amino acid.

5. The method of claim 1, wherein the reaction takes place in a polar aprotic solvent.

6. The method of claim 1, wherein the amino group is a piperazine group.

7. The method of claim 5, wherein the solvent is dimethyl formamide.

8. The method of claim 1, wherein the reaction takes place under standard temperature and pressure conditions.

* * * * *